United States Patent
Inoue et al.

(10) Patent No.: US 12,161,675 B2
(45) Date of Patent: Dec. 10, 2024

(54) PRODUCTION METHOD FOR CULTURE SUPERNATANT PREPARATION

(71) Applicant: LABORATORY OF CELL APPLIED TECHNOLOGIES, CO, Tokyo (JP)

(72) Inventors: Hajime Inoue, Kawasaki (JP); Chiharu Fujita, Kawasaki (JP)

(73) Assignee: Laboratory of Cell Applied Technologies, Co, Kanagawa (JP)

( * ) Notice: Subject to any disclaimer, the term of this patent is extended or adjusted under 35 U.S.C. 154(b) by 927 days.

(21) Appl. No.: 17/252,272

(22) PCT Filed: Aug. 2, 2019

(86) PCT No.: PCT/JP2019/030608
§ 371 (c)(1),
(2) Date: Dec. 14, 2020

(87) PCT Pub. No.: WO2020/027336
PCT Pub. Date: Feb. 6, 2020

(65) Prior Publication Data
US 2021/0260135 A1   Aug. 26, 2021

(30) Foreign Application Priority Data
Aug. 3, 2018   (JP) .................. 2018-146349

(51) Int. Cl.
*A61K 35/36* (2015.01)
*A61K 35/28* (2015.01)
*A61K 47/02* (2006.01)
*C12N 5/00* (2006.01)

(52) U.S. Cl.
CPC .............. *A61K 35/36* (2013.01); *A61K 35/28* (2013.01); *A61K 47/02* (2013.01); *C12N 5/0018* (2013.01)

(58) Field of Classification Search
CPC ........ A61K 35/36; A61K 35/28; A61K 47/02; C12N 5/0018; C12N 2502/09; C12N 2502/1364; C12N 2502/1382
See application file for complete search history.

(56) References Cited

U.S. PATENT DOCUMENTS

2013/0195991 A1 * 8/2013 Ueda ................ A61P 25/14
514/8.1

FOREIGN PATENT DOCUMENTS

| CN | 103037872 A | 4/2013 | |
|---|---|---|---|
| JP | WO1987/003284 A1 | 6/1987 | |
| JP | WO2008066199 A1 | 6/2008 | |
| JP | 2011-510662 A | 4/2011 | |
| JP | WO2017/110425 A1 | 6/2017 | |
| JP | 2017214321 A * | 12/2017 | |
| KR | 20170090549 A | 8/2017 | |
| WO | WO-2016210150 A1 * | 12/2016 | ............. A61K 35/28 |

OTHER PUBLICATIONS

Dulbecco's Modified Eagle's Medium (DMEM) Formulation. Datasheet [online]. Sigma, 2024 [retrieved Feb. 8, 2024]. <URL: https://www.sigmaaldrich.com/US/en/technical-documents/technical-article/cell-culture-and-cell-culture-analysis/mammalian-cell-culture/dulbecco-modified-eagle-medium-formulation> (Year: 2024).*
International Search Report of International Patent Application No. PCT/JP2019/030608 completed Sep. 25, 2019 and mailed Oct. 8, 2019 (4 pages).
Written Opinion of International Patent Application No. PCT/JP2019/030608 completed Sep. 25, 2019 and mailed Oct. 8, 2019 (7 pages).
Ntai A. et al., "Trehalose to cryopreserve human pluripotent stem cells", Stem Cell Res, Jul. 25, 2018, vol. 31, pp. 102-112.
2nd Office Action of Chinese Application No. 201980041197.4 issued Jun. 25, 2024 (8 pages).

* cited by examiner

Primary Examiner — Kara D Johnson
(74) Attorney, Agent, or Firm — Pyprus Pte Ltd; George D. Liu

(57) ABSTRACT

To provide a culture supernatant preparation which has excellent biocompatibility and contains a large quantity of specific genes or proteins. A method for producing the culture supernatant preparation including: a first culturing step of culturing cells to a confluent state using a first medium; a second culturing step of culturing the cells using a second medium that is different from the first medium after the first culturing step; and a culture supernatant preparation obtaining step of obtaining the culture supernatant preparation including the second medium after the second culturing step, the second medium including a calcium ion and a buffering agent.

11 Claims, No Drawings

PRODUCTION METHOD FOR CULTURE SUPERNATANT PREPARATION

TECHNICAL FIELD

The present invention relates to a method for producing a culture supernatant preparation and the like. Specifically, it relates to a method for producing a culture supernatant preparation which uses a culture supernatant obtained by culturing cells using an electrolytic solution such as an infusion liquid used for injection or intravenous drip infusion with little contamination of a cell culture medium.

BACKGROUND ART

A culture supernatant includes substances (secretions) secreted from cells when they are cultured. Thus, compositions (culture supernatant preparations) for treating or preventing various diseases included in the culture supernatant are considered to be effective for ameliorating various diseases and the like. For example, Japanese Patent No. 6296622 describes a method for producing a composition for treating a damaged part including a culture supernatant. Japanese Patent No. 6152205 describes an anti-allergic therapeutic composition including a culture supernatant.

CITATION LIST

Patent Literature

Patent Literature 1: Japanese Patent No. 6296622
Patent Literature 2: Japanese Patent No. 6152205

DESCRIPTION OF INVENTION

Technical Problem

On the other hand, these culture supernatant preparations include a medium in the final culturing step. Some types of media, for example, a serum-free medium and an animal-free medium, reduce components derived from organisms other than human. However, the medium itself is prepared for the purpose of culturing cells. Thus, administering the culture supernatant into a living body may cause a variety of problems. Thus, an object of the present invention is to provide a culture supernatant preparation having excellent biocompatibility. Further, the primary use of the medium is to culture cells, and it is not necessarily the use of the medium to administer the culture supernatant to a patient. Thus, as a preferable example of the present invention, an object of the present invention is to provide a culture supernatant preparation including a large quantity of specific genes or proteins.

Solution to Problem

The present invention is basically based on the finding that a culture supernatant preparation having excellent biocompatibility can be obtained by using an electrolyte solution such as an infusion liquid used for an injection agent, intravenous drip infusion, or the like as a medium in the final culturing step. Further, as is demonstrated by Examples below, the present invention is based on the finding that, when an infusion liquid is used instead of a normal cell culture medium, the culture supernatant includes a larger amount of certain types of genes or proteins and may exhibit higher therapeutic, preventive, and ameliorative effects in various cases.

The first invention disclosed in the present specification relates to a method for producing a culture supernatant preparation.

This method includes a first culturing step, a second culturing step, and a culture supernatant preparation obtaining step.

The first culturing step is a step of culturing cells to a confluent state using a first medium. The cells are preferably adipose tissue-derived mesenchymal stromal cells, epidermis-derived epithelial cells, or dental pulp-derived mesenchymal stem cells.

The second culturing step is a step of culturing cells using a second medium that is different from the first medium after the first culturing step.

The second medium is an electrolytic solution including a calcium ion and a buffering agent. The second medium may be an infusion liquid for injection or an infusion liquid for intravenous drip infusion. In the second culturing step, it is preferable that a $CO_2$ incubator is not used and $CO_2$ culturing is not performed. The second culturing step is preferably a step of culturing cells from 5 hours to 5 days. The second medium preferably further includes prostaglandin.

The culture supernatant preparation obtaining step is a step of obtaining a culture supernatant preparation including the second medium after the second culturing step. The culture supernatant preparation preferably includes the second medium after the second culturing step in an amount of 50 wt. % to 100 wt. %. The culture supernatant preparation obtaining step preferably includes a step of adding trehalose.

The method described above preferably further includes a culture supernatant recovery step of recovering the culture supernatant and a freezing step of freezing the culture supernatant recovered in the culture supernatant recovery step after the second culturing step. The culture supernatant preparation is preferably a raw material for cosmetics, medicines, foods, or drinks.

Another invention different from the above invention, disclosed in the present specification, relates to a culture supernatant preparation. This culture supernatant preparation is produced by any of the above methods.

That is, this culture supernatant preparation is produced by the method for producing the culture supernatant preparation including the first culturing step of culturing cells to a confluent state using the first medium and the second culturing step of culturing cells using the second medium that is different from the first medium after the first culturing step. Further, the culture supernatant preparation includes the second medium after the second culturing step in an amount of 50 wt. % or more and 100 wt. % or less, and the second medium includes a calcium ion and a buffering agent.

Another invention different from the above invention, disclosed in the present specification, is a liquid medicine functioning as a cell culture medium and an infusion liquid, and the liquid medicine includes a calcium ion, prostaglandin, and a buffering agent.

Advantageous Effects of Invention

According to the present invention, the culture supernatant preparation having excellent biocompatibility can be provided.

DESCRIPTION OF EMBODIMENTS

The following describes embodiments of the present invention. The present invention is not limited to the embodiments described below and includes modifications appropriately modified by a person skilled in the art in a range obvious from the embodiments below.

The first invention disclosed in the present specification relates to a method for producing a culture supernatant preparation. The culture supernatant preparation is a composition, a medicine, a cosmetic, or a dietary supplement which includes the culture supernatant as an active ingredient in an effective amount. This method includes a first culturing step, a second culturing step, and a culture supernatant preparation obtaining step.

The first culturing step is a step of culturing cells to a confluent state using a first medium. The cells may be derived from human, a non-human mammal, an insect, a bird, or a plant. The cells are preferably adipose tissue-derived mesenchymal stromal cells or epidermis-derived epithelial cells. In the first culturing step, a known culturing method is appropriately adopted.

The culturing method may appropriately be adjusted depending on cells to be cultured. As an example of a culture liquid, α-MEM or DMEM supplemented with 10 to 15% autoserum or fetal bovine serum (FBS) and antibiotics can be used. A medium free from a human- or animal-derived component may also be used. A growth factor, such as fibroblast growth factor (bFGF) or adrenomedullin, may be added as needed. Culturing can be performed under any condition suitable for culturing mammalian cells. In general, cells are cultured for several days at 37° C. and 5% $CO_2$, and the medium is replaced as needed.

The second culturing step is a step of culturing cells using a second medium that is different from the first medium after the first culturing step.

The second medium is an electrolytic solution including a calcium ion, a buffering agent, and the like. Further, the second medium preferably includes less sugar, and the content of the sugar (e.g., glucose) is preferably 1 g/l or less. It may be 0.8 g/l or less, 0.5 g/l or less, 0.1 g/L to 1.5 g/L, 0.1 g/L to 1.2 g/L, 0.1 g/L to 1 g/L, 0.5 g/L to 1.2 g/L, or 0.8 g/L to 1.1 g/L.

The calcium ion included in the second medium is preferably 0.045 mM to 1.802 mM. It may be 0.074 mM to 1.505 mM, 0.045 mM to 2 mM, 0.180 mM to 2 mM, 1 mM to 2 mM, 1.3 mM to 1.8 mM, 1.2 mM to 1.6 mM, 1 mM to 1.6 mM, 0.045 mM to 1.352 mM, 0.180 mM to 0.901 mM, or 20 mg/l to 100 mg/l. Examples of a salt included in the second medium include NaCl, KCl, and $CaCl_2$), and the salt may be included in an amount of 1 g/L to 30 g/L, 4 g/L to 30 g/L, or 6 g/L to 11 g/L Examples of the buffering agent include $MgSO_4·7H_2O$, $Na_2HPO_4$, $KH_2PO_4$, and hydroxyethylpiperazine ethane sulfonic acid. These may be used in combination with other salts (e.g., sodium hydrogen carbonate, sodium carbonate, pyruvic acid, citric acid, salts thereof, and the like). The content of these buffering agents is preferably 1 mg/l to 5 g/l, and it may be 2 mg/l to 500 mg/l or 10 mg/l to 300 mg/l.

The acidity of the second medium is, for example, pH5.5 to pH9, and it may also be pH7.2 to pH7.8. Further, the second medium preferably includes less or no amino acids, and the amino acid content is preferably 1 mg/ml or less, preferably 0.8 mg/l or less, further preferably 0.5 mg/l or less. The second medium preferably includes less or no vitamins, and the content of the vitamins is preferably 1 mg/ml or less, preferably 0.8 mg/l or less, further preferably 0.5 mg/l or less. The second medium is preferably free from an antibiotic (e.g., penicillin), a growth factor, and a cytokine. The second medium preferably includes less or no heavy metal elements such as iron, copper, and lead and trace elements. Having the small amounts of such elements makes it possible to prevent the synthesis of metalloproteins and promote the synthesis of growth factors. The second medium is preferably free from a carcinogenic substance such as a polyamine (e.g., Putrescine 2HCl). The second medium is preferably free from a purine base. Having no purine base in the second medium makes it possible to activate a salvage pathway of nucleic acids.

Having no or small amounts of vitamins and amino acids in the second medium makes it possible to increase the synthesis of growth factors by promoting autophagy.

The second medium can maintain a stable environment during culturing in a general culturing environment (e.g., the second medium can reduce fluctuation of the acidity and maintains the buffering capacity during culturing, making it unnecessary to perform $CO_2$ culturing or the like).

The second medium preferably has the higher water content as compared with a normal medium. For example, the water content is preferably 95 wt. % to 99.99 wt. %, when the second medium is taken as 100 wt. %. It may be 96 wt. % to 99.9 wt. % or 97 wt. % to 99.9 wt. %. Having the higher water content in the medium can reduce the osmotic pressure. For example, when cells are grown by adherent culture, the cells are usually detached from a culture container by using an animal-derived digestive enzyme such as trypsin. Using the second medium eliminates the necessity of using a digestive enzyme. This can reduce side effects such as infection caused by an animal-derived component when an agent including the second medium is administered to a patient.

The second medium may be composed of only sugar (e.g., glucose), salts (salts including a calcium ion source, e.g., the ones composed of only NaCl, KCl, and $CaCl_2$), or salts including these as main salts), and buffering agents (e.g., buffering agents composed of only $MgSO_4·H_2O$, $Na_2HPO_4·2H_2O$, $KH_2PO_4$, $NaHCO_3$, and HEPES, or buffering agents including these as main buffering agents) with the remainder being a solvent (e.g., water). The second medium having such a composition causes the high expression of specific genes or proteins and functions as a medium and an infusion liquid having excellent biocompatibility, as the effectiveness of the second medium is confirmed by Examples below.

The second medium may be an infusion liquid for injection or an infusion liquid for intravenous drip infusion. In this case, a product manufactured and sold as an infusion liquid for injection or an infusion liquid for intravenous drip infusion can be appropriately used. Examples of the infusion liquid for injection include a sugar liquid agent, an extracellular fluid replacement fluid (a physiological saline solution, a Ringer's solution, a Ringer's lactate solution, an extracellular fluid replacement fluid, a Ringer's acetate solution, a Ringer's bicarbonate solution), a hypotonic electrolyte fluid, an amino-acid preparation (a high-concentration amino acid solution, an amino acid solution for renal failure, an amino acid solution for liver failure, an amino acid solution for child), peripheral parenteral nutrition (PPN), total parenteral nutrition (TPN), fat emulsion, and a plasma volume expander. Of these, an extracellular fluid replacement fluid (a physiological saline solution, a Ringer's solution, a Ringer's lactate solution, an extracellular fluid replacement fluid, a Ringer's acetate solution, a Ringer's bicarbonate solution) and an isotonic electrolyte fluid are preferable. Specific examples of the infusion liquid include PAREPLUS (registered trademark).

The second medium having the low amino acid content avoids an interaction (mainly oxidation and reduction) and a polymerization reaction with synthesized and secreted growth factors, thereby making it possible to prevent deterioration of the components and also moisture absorption and deterioration caused by the contaminated amino acids. Further, the low amino acid content in the second medium reduces the risk of bacteria growth when the second medium is used as a raw material for cosmetics, making it possible to ensure the preservability of products without adding a preservative or an antioxidant. The second medium free from amino acids does not require a step of removing amino acids when applied to an affected site, and the second medium does not serve as nutrients for growing bacteria or the like residing in an affected site. This means that the second medium does not cause malodor when applied to a wound surface. Further, after the second medium is formulated, an agent including the second medium does not cause dysgeusia or body odor when applied by intravenous drip infusion, thus the second medium is highly convenient when it is used as a cosmetic or a medicine. Desalting can be easily performed with the second medium free from amino acids. This makes it easy to obtain a high-concentration dried growth factor product by freeze drying when cells are grown in mass culture. When a normal medium is used, the medium needs to be exchanged after 48 to 72 hours under any circumstance. In a case where the second medium is not an amino acid-containing medium, the living environment can be maintained for a long period of time (e.g., about 7 days) by suppressing metabolic activity of the cultured cells stored in a cold place at 4° C. Subsequently, the cells can be propagated again by exchanging the medium. The second medium including a calcium ion and a buffering agent preferably has a simple composition. Thus, the second medium having high versatility can be applied to any types of animal cells (including ES cells, iPS cells, and stem cells) and plant cells (in particular, callus culture of plants and maintenance of plant stem cells).

In the second culturing step, it is preferable that a $CO_2$ incubator is not used and $CO_2$ culturing is not performed. That is, culturing is preferably performed using a culture container without performing $CO_2$ incubation. The second culturing step is preferably a step of culturing cells from 5 hours to 5 days (from 10 hours to 2 days or from 5 hours to 3 days). Culturing may be performed by adhesion culture or suspension culture depending on cells to be cultured. In a case where the cells are removed, culturing may be performed by a method in which the cells are easily removed.

The culture supernatant preparation obtaining step is a step of obtaining a culture supernatant preparation including the second medium after the second culturing step. The culture supernatant preparation preferably includes the second medium after the second culturing step in an amount of 50 wt. % to 100 wt. %. The culture supernatant preparation may include the second medium (including the culture supernatant) after the second culturing step in an amount of 60 wt. % to 100 wt. %, preferably in an amount of 70 wt. % to 99 wt. %, 70 wt. % to 90 wt. %, 80 wt. % to 99 wt. %, 90 wt. % to 100 wt. %, or 90 wt. % to 95 wt. % As the culture supernatant of stem cells or the like, a supernatant component, which is obtained by subjecting the culture supernatant to solid-liquid separation by centrifugal separation, is usually used. In the method described in this specification, the second medium can be actively included in a preparation, allowing a filtrate simply obtained by filtering the medium after the second culturing step to be used.

The culture supernatant preparation may be a treated material obtained by removing the water content by freeze drying from the culture supernatant obtained as described above, a treated material obtained by concentrating the culture supernatant under a reduced pressure using an evaporator or the like, a treated material obtained by concentrating the culture supernatant using an ultrafiltration membrane or the like, a treated material obtained by subjecting the culture supernatant to solid-liquid separation using a filter, or the original liquid of the culture supernatant not subjected to the above treatments. Further, for example, the sterile culture supernatant may be obtained by subjecting the supernatant of the cell culture to centrifugal separation (e.g., 1,000×g, 10 minutes), fractionating the supernatant using ammonium sulfate (e.g., saturated 65% ammonium sulfate), suspending a precipitate using an appropriate buffer solution, subjecting the resulting product to a dialysis treatment, and filtering the resulting dialysate using a syringe filter (e.g., 0.2 μm). The culture supernatant thus collected can be used as it is, or it can be frozen, stored and thawed when used. Further, the culture supernatant may be added with a pharmaceutically acceptable carrier and aliquoted into sterilized containers in a liquid amount of, for example, 0.2 ml or 0.5 ml for easy handling. Further, the culture supernatant may be treated with a virus clearance filter or Y-ray irradiation as a countermeasure against risks of infectious pathogens.

As described above, the culture supernatant recovery step of recovering the culture supernatant and the freezing step of freezing the culture supernatant recovered in the culture supernatant recovery step may be included after the second culturing step. For freezing the culture supernatant, for example, the culture supernatant is cooled from −200° C. to 0° C., and it may be cooled from −100° C. to −5° C.

Note that the culture supernatant preparation may be obtained by disrupting the cells after the second culturing step, performing centrifugal separation, and then filtering the supernatant using a filter, or it may be obtained by further freezing and drying the filtrate thus obtained.

The culture supernatant preparation (an agent of the present invention) may be produced by a method known to a person skilled in the art. The agent of the present invention can be produced as an oral preparation and a parenteral preparation. However, it is preferably produced as a parenteral preparation. Such a parenteral preparation may be prepared as a liquid agent (an aqueous liquid agent, a nonaqueous liquid agent, a suspended liquid agent, an emulsified liquid agent, or the like) or as a solid agent (a powder filling preparation, a freeze-dried preparation, or the like). Alternatively, the agent of the present invention may be prepared as a sustained-release preparation. A liquid agent is preferable as a dosage form in a case where living cells are used as an agent, while both a liquid agent and a solid agent can be selected as a dosage form in a case where partial components of the cells or the whole dead cells are used as an agent.

The agent including the culture supernatant as an active ingredient is known as disclosed in, for example, JP-A-2013-18756, Japanese Patent No. 5139294, and Japanese Patent No. 5526320. Thus, the agent including the culture supernatant of the present invention can be produced by using a known method.

As a dosage form of the culture supernatant according to the present invention, both a liquid agent and a solid agent can be selected. For a biopharmaceutical including proteins as a main agent, powder formulation having excellent storage stability is often selected due to a problem of preservability. The culture supernatant of the present invention is also desirably produced as a solid agent for improving preservability and a storage period.

The agent including the culture supernatant of the present invention can be administered by using a known administration method such as intravenous administration, intraarterial administration, intramuscular administration, subcutaneous administration, intraperitoneal administration, intranasal administration, intrathecal administration, intraarticular administration, intragingival administration, or patching. The agent of the present invention may be directly administered to the affected site or the target site. Further, the agent of the present invention may be administered by opening the affected site by a surgical operation, or it can be noninvasively administered using an endoscope and a catheter. Any optimal administration method can be employed in accordance with target diseases. In a case of selecting intravenous injection as a transplanting method, the culture supernatant is administered in an amount of preferably 0.1 mL to 1,000 mL, more preferably 30 mL to 300 mL, as an administration unit.

The liquid agent can be produced by a known method. For example, it can be produced by mixing mesenchymal stem cells with a pharmaceutically acceptable solvent and filling the resulting mixture in a sterilized container for liquid agent. Examples of the pharmaceutically acceptable solvent include water for injection, distilled water, physiological saline, an electrolyte solution agent, or a liquid agent having a composition equivalent to that of a culture liquid, and a sterilized solvent is preferably used. Examples of the sterilized container for liquid agent include an ampoule, a vial, a syringe, and a bag. For those containers, a known container made of glass, plastic, or the like can be used. Specific examples of the plastic-made container include a container made by using a material such as polyvinyl chloride, polyethylene, polypropylene, or a copolymer of ethylene and vinyl acetate. Examples of a sterilizing method of these containers and solvents include a heating method (a flame method, a drying method, a high-temperature steam method, a free-flowing steam method, a boiling method, or the like), a filtration method, an irradiation method (a radiation method, an ultraviolet method, a high-frequency method, or the like), a gas method, and a liquid chemical method. These sterilizing methods can be appropriately selected and used by a person skilled in the art depending on the material of the container and the characteristics of the solvent.

Note that the present specification also discloses a preparation including cultured cells. In a case where cells are used for treatment as a liquid agent, intravenous injection can be most frequently used as a transplanting method. For example, in the case of using intravenous injection, the liquid agent is prepared preferably $1 \times 10^5$ cells/mL to $5 \times 10^7$ cells/mL, more preferably $1 \times 10^6$ cells/mL to $1 \times 10^7$ cells/mL. Further, a mesenchymal stem cell agent is prepared preferably $1 \times 10^5$ cells to $1 \times 10^9$ cells, more preferably $2 \times 10^7$ cells to $2 \times 10^8$ cells, as an administration unit of the intravenous injection for human. As for other administration routes, the preparation can be used within a range of the liquid quantity which can be transplanted to the tissue and the maximum number of cells which can be suspended in that liquid quantity.

As a method for producing the solid agent, for example, a freeze-drying method, a spray drying method, or a sterile recrystallization method can be used.

The agent including the cells can be administered by using a known administration method such as intravenous administration, intraarterial administration, intramuscular administration, subcutaneous administration, intraperitoneal administration, intranasal administration, intrathecal administration, intraarticular administration, or intragingival administration. A preferable example of an administration form is administration by injection, and, in a case of intravenous administration, the agent of the present invention may also be injected by intravenous drip infusion.

The cells may be prepared with a pharmaceutically acceptable carrier or medium. Examples of the pharmaceutically acceptable carrier or medium include a pharmaceutically acceptable substance such as an excipient, a stabilizer, a solubilizer, an emulsifier, a suspending agent, a buffering agent, a tonicity agent, an antioxidant, or a preservative. Further, a high-polymer material such as polyethylene glycol (PEG) and a conjugated compound such as cyclodextrin can be used. Examples of the excipient include a substance having no pharmacological effect by itself such as starch or lactose. Examples of the stabilizer include albumin, gelatin, sorbitol, mannitol, lactose, sucrose, trehalose, maltose, and glucose. Of these, sucrose or trehalose is preferable. Examples of the solubilizer include ethanol, glycerin, propylene glycol, and polyethylene glycol. Examples of the emulsifier include lecithin, aluminum stearate, or sorbitan sesquioleate. Examples of the suspending agent include macrogol, poly vinyl pyrrolidone (PVP), or carboxymethyl cellulose (CMC). Examples of the tonicity agent include sodium chloride and glucose. Examples of the buffering agent include a citrate, an acetate, boric acid, and a phosphate. As an aqueous medium for suspending cells, for example, an aqueous solution for injection or the like in which the osmotic pressure and pH are adjusted to near the blood values and the salt concentration or the like is adjusted is appropriately used. For example, a Ringer's solution such as a Ringer's acetate solution or a sugar containing Ringer's acetate solution and other infusion liquids, physiological saline, a glucose solution, or the like can be used without being limited thereto. For example, in a case of using a Ringer's solution for infusion, a Ringer's solution may be added with an acceptable amount of dimethyl sulfoxide (DMSO) or human serum albumin (HSA). Examples of the antioxidant include ascorbic acid, sodium hydrogen sulfite, and sodium metabisulfite. Examples of the preservative include phenol, thimerosal, and benzalkonium chloride.

For the purpose of treating various diseases and improving various abilities of subjects (human or non-human mammals), the present invention also provides a method including a step of administering the culture supernatant (or cultured cells, purified products derived from cultured cells) to the subjects.

Another invention different from the above invention, disclosed in the present specification, is a liquid medicine functioning as a cell culture medium and an infusion liquid, and the liquid medicine includes a calcium ion, prostaglandin, and a buffering agent. As the liquid medicine, the second medium described above is appropriately adopted.

As described in Japanese Patent No. 6497827, the culture supernatant functions as an eicosanoid production promoter. This agent is preferably a therapeutic agent for arteriosclerosis or diabetes. Japanese Patent No. 6250196 describes that a PPAR agonist serves as a therapeutic agent for diabetes. Japanese Patent No. 4515026 shows that activation of PPARγ is effective for treating diabetes. Japanese Patent No. 6157041 shows that a PPARγ activator is effective for treating arteriosclerosis and diabetes. The agent of the present invention, which activates PPARγ, is effective for treating arteriosclerosis and diabetes. This agent is preferably a therapeutic agent for articular rheumatism. It is known that, in a model of articular rheumatism, 15-deoxy-delta-12,14-prostaglandin J2 reduces the rheumatism clinical score, pain, and edema (Mediators Inflamm. 2016; 2016:9626427. Epub 2016 Oct. 31). The agent of the present invention promotes production of an eicosanoid, for example, 15-deoxy-delta-12,14-prostaglandin J2, as an activator of PPARγ from macrophage, thus it is effective for treating articular rheumatism. This agent is preferably a preventive agent or a therapeutic agent for prostate cancer, stroke, or cerebral dysfunction. It is reported, for example, in Cancer Res. 2001 Jan. 15; 61 (2): 497-503, that 15-HETE suppresses the growth of the prostate cancer cell line (PC3) and has inhibitory effects on multiple carcinomas. Further, it is reported, in J Lipid Res. 2015 March; 56 (3): 502-14, that administration of 15-HETE reduces a degree of the brain tissue dysfunction and the inflammatory response in the brain after cerebral ischemia in a stroke model. The agent of the present invention promotes production of an eicosanoid, for example, 15-hydroxyeicosatetraenoic acid (15-HETE), as an activator of PPARγ from macrophage, thus it is effective for treating prostate cancer. Japanese Patent No. 5940261 describes that an activator of the peroxisome proliferator-activated receptor (PPARγ) prevents and ameliorates at least one of hypertension, insulin-resistant diseases, stroke, Alzheimer's disease, and neurological disorders. The agent of the present invention, which activates PPARγ, is effective for preventing and treating stroke and the cerebral dysfunction. This agent is preferably a preventive agent or a therapeutic agent for pain. For example, it is shown, in Exp. Ther. Med. 2016 October; 12 (4): 2644-2650, that administration of pioglitazone known as an activator of PPARγ suppresses activated microglia in neuropathic pain, resulting in lowering the pain threshold for mechanical stimuli. The agent of the present invention promotes production of an eicosanoid, for example, 15-deoxy-delta-12, 14-prostaglandin J2, as an activator of PPARγ from macrophage, thus it is effective for preventing or treating pain.

Japanese Patent No. 6132459 describes a preventive and therapeutic agent for enteritis including the culture supernatant of mesenchymal stem cells. Thus, the agent including the culture supernatant of the present invention is effective for preventing and treating enteritis.

Example 1

Cell Culture and Recovery of Culture Supernatant

Adipose tissue-derived mesenchymal stromal cells extracted by subjecting normal human adipose tissues to an enzyme treatment were cultured using a DME medium (Dulbecco's modified eagle medium manufactured by Gibco, high glucose) including 20% fetal bovine serum (FBS) in a non-treated culture flask (manufactured by FALCON) as primary culture. The primary culture cells right before confluency were recovered by an enzyme treatment, seeded on a non-treated 12-well culture plate (manufactured by Sumitomo Bakelite Co., Ltd.) using the same medium, and cultured until becoming confluent.

After confirming that the cells became confluent, the medium was removed and the cell surface was rinsed with PBS (Dulbecco's phosphate buffered saline manufactured by DS Pharma Biomedical Co., Ltd.).

After rinsing the cells, the medium was replaced with an FBS-free DME medium or HBSS (Hanks' balanced salt solution manufactured by Sigma-Aldrich Co.)-HEPES. Subsequently, 12 wells were divided into 4 groups each consisting of 3 wells, and the FBS-free DME medium was cultured in a 5% $CO_2$ incubator (Reference example) and HBSS-HEPES was cultured in an incubator (Example). The culture supernatant in each well was recovered immediately after replacement (0 hours) and 3 hours, 6 hours, 24 hours, and 48 hours thereafter.

The FBS-free DME medium is a Dulbecco's modified eagle medium free from FBS. The DME medium contains various components such as glucose and L-glutamine.

The HBSS (Hanks' balanced salt solution) is (1) an sodium hydrogen carbonate solution as an isotonic solution, (2) a buffer solution including NaCl, KCl, $MgSO_4 \cdot 7H_2O$, $Na_2HPO_4$, glucose, and $KH_2PO_4$, and (3) a $CaCl_2$) solution and a buffer solution. HEPES, which is hydroxyethylpiperazine ethane sulfonic acid, serves as a buffering agent or a pH adjuster.

The sugar content included in the FBS-free DME medium was 4.5 g/L, the total amount of amino acids (L-glutamic acid, etc.) was 1.6 g/L, and a calcium ion was 1.8 mM.

On the other hand, the sugar content included in the HBSS-HEPES medium (hanks-HEPES pH7.4) was 1.0 g/L, NaCl at 8.0 g/L, KCl at 0.4 g/L, $CaCl_2$ at 0.14 g/L, $MgSO_4 \cdot H_2O$ at 0.2 g/L, $Na_2HPO_4 \cdot 2H_2O$ at 0.06 g/L, $KH_2PO_4$ at 0.06 g/L, $NaHCO_3$ at 0.35 g/L, HEPES pH7.4 at 20 mM. The total amount of amino acids (L-glutamic acid, etc.) was 0 g/L and a calcium ion was 1.5 mM.

Measuring Method of Gene Expression Level

After recovering the culture supernatant as described above, an RNA extraction solution ISOGEN (Nippon Gene Co., Ltd., No. 319-90211) was added to each well in an amount of 400 microliters and the total RNAs were extracted from the cells in accordance with a conventional method. The precipitate of the total RNAs obtained by using Ethachinmate (Nippon Gene Co., Ltd., No. 312-01791) was dissolved in nuclease-free water. The concentration of the total RNAs was measured using 1.5 microliters of the dissolved RNAs by NanoDrop (Thermo Fisher Scientific). One hundred nanograms of the total RNAs thus obtained were used to synthesize complementary DNA using an iScript cDNA synthesis kit (Bio-Rad Laboratories, Inc., No. 1708891), and the resulting complementary DNA was used for quantifying an expression level of each gene by real-time PCR (Rotor-Gene Q manufactured by QIAGEN).

Quantification of Gene Expression by Real-Time PCR Method

The synthesized DNA, primers (QuantiTect Primer Assay, QIAGEN) specific for the gene to be detected and quantified, and a real-time PCR agent (RotorGene SYBR Green, QIAGEN) were mixed, and real-time PCR was performed by using the Rotor-Gene Q system (QIAGEN) to amplify fragments of the gene to be detected and quantified. In this operation, primers specific for β-Actin as a housekeeping gene were used for amplification in the same manner, and this amplification curve was used as a reference to relatively calculate a quantitative value of the gene desired to be detected and quantified.

The following primer mix solutions from QIAGEN were used as the primers specific for each gene.

Human β-Actin
    Hs_ACTB_1_SG catalog number QT00095431
Human FGF2
    Hs_FGF2_1_SG catalog number QT00047579
Human VEGFA
    Hs_VEGFA_1_SG catalog number QT01010184

Quantification Method of Proteins Included in Culture Supernatant

The culture supernatant recovered as described in cell culture and recovery of culture supernatant was passed through a filter having a diameter of 0.22 micrometers to prepare a sample for protein quantification.

Protein quantification of the sample was performed by using the QUANTIKINE ELISA (Human VEGF, FGF-2) kit from R&D Systems, Inc. and a quantitative value of each protein was obtained in accordance with the protocol of the kit.

The results are shown in Table 1 and Table 2.

TABLE 1

VEGF

| Solutions | Time | Value of intracellular mRNA expression quantification | Amounts of secreted extracellular protein |
| --- | --- | --- | --- |
| — | 0 | 1.0 | 0.0 |
| DME(H) | 6 | 0.7 | 8.4 |
| DME(H) | 24 | 1.2 | 28.1 |
| DME(H) | 48 | 2.3 | 56.7 |
| Hanks-HEPESpH 7.4 | 6 | 1.1 | 8.9 |
| Hanks-HEPESpH 7.4 | 24 | 3.8 | 29.6 |
| Hanks-HEPESpH 7.4 | 48 | 7.5 | 72.7 |

TABLE 2

FGF-2

| Solutions | Time | Value of intracellular mRNA expression quantification | Amount of secreted extracellular protein amounts |
| --- | --- | --- | --- |
| — | 0 | 1.0 | 0.0 |
| DME(H) | 6 | 0.4 | 19.1 |
| DME(H) | 24 | 0.4 | 118.0 |
| DME(H) | 48 | 0.8 | 82.3 |
| Hanks-HEPESpH 7.4 | 6 | 0.7 | 0.0 |
| Hanks-HEPESpH 7.4 | 24 | 1.4 | 0.0 |
| Hanks-HEPESpH 7.4 | 48 | 1.4 | 6.5 |

Results of Real-Time PCR

The expression level of the VEGF gene in the cells was highest in the Hanks-HEPES solution.

The expression level of the FGF-2 gene in the cells was highest in the Hanks-HEPES solution.

Result of Protein Quantification

The amount of VEGF in the culture supernatant was highest in the Hanks-HEPES solution.

The amount of FGF-2 in the culture supernatant was highest in the DME medium.

Discussion

Both the gene expression level and the protein amount in the culture supernatant tended to increase over time at 0, 6, 24, and 48 hours. The expression level of the VEGF gene and the protein amount in the culture supernatant were the highest in the Hanks-HEPES solution (Example). The expression level of the FGF-2 gene was the highest in the Hanks-HEPES solution, while the protein amount in the culture supernatant was higher in the DME (H) (Reference example).

Example 2

Cell Culture and Recovery of Culture Supernatant

Epidermal keratinocytes extracted by subjecting normal human skin tissues to an enzyme treatment were cultured using a serum-free cell culture medium (No. MEPI500CA manufactured by Gibco) containing Supplement S7 (No. S0175 manufactured by Gibco) in a non-treated culture flask (manufactured by FALCON) as primary culture. The primary culture cells right before confluency were recovered by an enzyme treatment, seeded on a non-treated 12-well culture plate (manufactured by Sumitomo Bakelite Co., Ltd.) using the same medium, and cultured until becoming confluent.

After confirming that the cells became confluent, the medium was removed and the cell surface was rinsed with PBS (Dulbecco's phosphate buffered saline manufactured by DS Pharma Biomedical Co., Ltd.) and the medium was replaced with a serum-free cell culture medium (EpiLife: Reference example) not containing Supplement 7 or an HBSS-HEPES pH7.4 solution (Example). Subsequently, 12 wells were divided into 4 groups each consisting of 3 wells, and the culture supernatant in each well was recovered immediately after replacement (0 hours) and 3 hours, 6 hours, and 24 hours thereafter.

The sugar content included in the serum-free cell culture medium (EpiLife: Reference example) not containing Supplement 7 was 1.0 g/L, the total amount of amino acids (L-glutamic acid, etc.) was 1.5 g/L, and a calcium ion was 8.4 mg/L.

Measuring Method of Gene Expression Level

After recovering the culture supernatant as described above, an RNA extraction solution ISOGEN (Nippon Gene Co., Ltd., No. 319-90211) was added to each well in an amount of 400 microliters and the total RNAs were extracted from the cells in accordance with a conventional method. The precipitate of the total RNAs obtained by using Ethachinmate (Nippon Gene Co., Ltd., No. 312-01791) was dissolved in nuclease-free water. The concentration of the total RNAs was measured using 1.5 microliters of the dissolved RNAs by NanoDrop (Thermo Fisher Scientific). One hundred nanograms of the total RNAs thus obtained were used to synthesize complementary DNA using an iScript cDNA synthesis kit (Bio-Rad Laboratories, Inc., No. 1708891), and the complementary DNA was used for quantifying an expression level of each gene by real-time PCR (Rotor-Gene Q manufactured by QIAGEN).

Quantification of Gene Expression by Real-Time PCR Method

The synthesized DNA, primers (QuantiTact Primer Assay, QIAGEN) specific for the gene to be quantified, and a real-time PCR agent (Rotor-Gene SYBR Green, QIAGEN) were mixed, and real-time PCR was performed by using the Rotor-Gene Q system (QIAGEN) to amplify fragments of the gene to be detected and quantified. In this operation, primers specific for β-Actin as a housekeeping gene were used for amplification in the same manner, and this amplification curve was used as a reference to relatively calculate a quantitative value of the gene desired to be detected and quantified.

The following primer mix solutions from QIAGEN were used as the primers specific for each gene.

Human β-Actin
  Hs_ACTB_1_SG catalog number QT00095431
Human EGF
  Hs_EGF_1_SG catalog number QT00051646
Human VEGFA
  Hs_VEGFA_1_SG catalog number QT01010184
Human FGF2
  Hs_FGF2_1_SG catalog number QT00047579

Quantification Method of Proteins Included in Culture Supernatant

The culture supernatant recovered as described in cell culture and recovery of culture supernatant was passed through a filter having a diameter of 0.22 micrometers to prepare a sample for protein quantification.

Protein quantification of the sample was performed by using the QUANTIKINE ELISA (Human VEGF) kit from R&D Systems, Inc. and a quantitative value of each protein was obtained in accordance with the protocol of the kit. The results are shown in Table 3 to Table 5.

TABLE 3

EGF

| Solutions | Time | Value of intracellular mRNA expression quantification |
|---|---|---|
| — | 0 | 1.0 |
| EpiLife | 3 | 1.4 |
| EpiLife | 6 | 2.3 |
| EpiLife | 24 | 3.9 |
| Hanks-HEPESpH 7.4 | 3 | 2.2 |
| Hanks-HEPESpH 7.4 | 6 | 2.9 |
| Hanks-HEPESpH 7.4 | 24 | 12.6 |

TABLE 4

VEGF

| Solutions | Time | Value of intracellular mRNA expression quantification | Amount of secreted extracellular protein |
|---|---|---|---|
| — | 0 | 1.0 | 0.0 |
| EpiLife | 3 | 1.5 | 28.7 |
| EpiLife | 6 | 1.3 | 66.7 |
| EpiLife | 24 | 8.5 | 394.7 |
| Hanks-HEPESpH 7.4 | 3 | 6.0 | 38.5 |
| Hanks-HEPESpH 7.4 | 6 | 10.8 | 202.4 |
| Hanks-HEPESpH 7.4 | 24 | 9.9 | 2442.5 |

TABLE 5

FGF-2

| Solutions | Time | Value of intracellular mRNA expression quantification |
|---|---|---|
| — | 0 | 1.0 |
| EpiLife | 3 | 2.9 |
| EpiLife | 6 | 1.5 |
| EpiLife | 24 | 5.3 |
| Hanks-HEPESpH 7.4 | 3 | 4.5 |
| Hanks-HEPESpH 7.4 | 6 | 9.6 |
| Hanks-HEPESpH 7.4 | 24 | 19.7 |

Result of Real-Time PCR

The expression level of the EGF gene in the cells was higher in the Hanks-HEPES solution (Example) than in the EpiLife medium (Reference example). The expression level of the FGF-2 gene in the cells was higher in the Hanks-HEPES solution than in EpiLife.

The expression level of the VEGF gene in the cells was higher in the Hanks-HEPES solution than in EpiLife. As a result of protein quantification, the amount of VEGF in the culture supernatant was higher in Hanks-HEPES.

Example 3

The culture liquid of adipose tissue-derived mesenchymal stromal cells having reached confluence was replaced with three kinds of solutions and an expression level of each of mRNAs in the cells was quantified after 48 hours. The solutions used for replacement was an FBS-free DME medium, a HBSS-HEPES medium and a PAREPLUS infusion liquid. The quantification result of the mRNA expression level is shown in Table 6.

PAREPLUS referring to the PAREPLUS infusion liquid includes glucose, sodium chloride, L-sodium lactate, calcium chloride hydrate, magnesium sulfate hydrate, zinc sulfate hydrate, thiamine chloride hydrochloride, pyridoxine hydrochloride, cyanocobalamin, panthenol, glacial acetic acid, an amino acid, an electrolyte, a stabilizer, and a pH adjuster.

TABLE 6

| Genes | Solutions | Time | Value of intracellular mRNA expression quantification |
|---|---|---|---|
| EDN1 | — | 0 | 1.0 |
|  | DME(H) | 48 | 2.5 |
|  | Hanks-HEPESpH 7.4 | 48 | 2.9 |
|  | PAREPLUS | 48 | 6.8 |
| EGF | — | 0 | 1.0 |
|  | DME(H) | 48 | 0.5 |
|  | Hanks-HEPESpH 7.4 | 48 | 1.1 |
|  | PAREPLUS | 48 | 1.4 |
| FGF2 | — | 0 | 1.0 |
|  | DME(H) | 48 | 2.3 |
|  | Hanks-HEPESpH 7.4 | 48 | 3.0 |
|  | PAREPLUS | 48 | 3.1 |
| PGES | — | 0 | 1.0 |
|  | DME(H) | 48 | 3.5 |
|  | Hanks-HEPESpH 7.4 | 48 | 5.3 |
|  | PAREPLUS | 48 | 2.1 |
| TGFb | — | 0 | 1.0 |
|  | DME(H) | 48 | 0.9 |
|  | Hanks-HEPESpH 7.4 | 48 | 1.6 |
|  | PAREPLUS | 48 | 0.6 |
| VEGF | — | 0 | 1.0 |
|  | DME(H) | 48 | 0.6 |
|  | Hanks-HEPESpH 7.4 | 48 | 1.8 |
|  | PAREPLUS | 48 | 1.1 |

It is found from Table 6 that the gene expression level is higher in the electrolyte solution (Hanks-HEPES, PAREPLUS) than in the medium (DME(H)). It is found that Hanks-HEPES is more preferable between the electrolyte solutions.

Example 4

The culture liquid of adipose tissue-derived mesenchymal stromal cells having reached confluence was replaced with the following solutions and an expression level of each of mRNAs in the cells was quantified after 48 hours.

TABLE 7

VEGF

| Solutions | Time | Value of intracellular mRNA expression quantification |
|---|---|---|
| DME(H) | 48 | 1.0 |
| HBSS-HEPES pH 7.4 | 48 | 3.6 |

TABLE 7-continued

VEGF

| Solutions | Time | Value of intracellular mRNA expression quantification |
|---|---|---|
| HBSS | 48 | 1.0 |
| KN No. 2 + Ca | 48 | 1.1 |
| PAREPLUS + Ca | 48 | 3.3 |

KN No. 2 refers to a KN No. 2 infusion liquid. The KN No. 2 infusion liquid includes sodium chloride, potassium chloride, L-sodium lactate, magnesium chloride, sodium dihydrogen phosphate monohydrate, dipotassium phosphate, and glucose.

TABLE 8

FGF-2

| Solutions | Time | Value of intracellular mRNA expression quantification |
|---|---|---|
| DME(H) | 48 | 1.0 |
| HBSS-HEPES pH 7.4 | 48 | 2.2 |
| HBSS | 48 | 0.3 |
| KN No. 2 + Ca | 48 | 2.3 |
| PAREPLUS + Ca | 48 | 3.6 |

It is found that, by comparing HBSS-HEPES pH7.4 and HBSS, adding HEPES pH7.4 promotes the gene expression by slowing down a pH shift to acidic.

Example 5

Recovery of Culture Supernatant and Freeze Drying

The culture supernatant after 48 hours in the second culturing step was recovered in a 50 mL centrifuge tube (Sumitomo Bakelite Co., Ltd.) and then subjected to centrifugal separation (740G, 5 minutes). The resulting supernatant was passed through a filtration filter (KURABO INDUSTRIES Ltd.) having a membrane pore diameter of 0.2 micrometers and aliquoted into syringes (Terumo Corp.). The syringes were sealed in sterile bags, frozen in a −80° C. freezer, and then transferred to the inside of the freeze-drying device (Yamato Scientific Co., Ltd.) to perform freeze drying. After the completion of freeze drying, the syringes were sealed with luer caps for syringe (Terumo Corp.).

Example 6

As was in Example 1, after confirming that the adipose tissue-derived mesenchymal stromal cells became confluent, the medium was removed and the cell surface was rinsed with PBS.

After rinsing the cells, the medium was replaced with HBSS-HEPES. Subsequently, 12 wells were divided into 6 groups each consisting of 2 wells and HBSS-HEPES was cultured in an incubator (Example). The total RNAs were extracted from the cells in each well immediately after replacement (0 hours) and 1 day, 2 days, 3 days, 4 days, 5 days, and 6 days thereafter using ISOGEN (manufactured by Nippon Gene Co., Ltd.), and the expression of the VEGF gene was relatively quantified by real-time PCR. The result is shown in Table 9. As shown in Table 9, it was found that the gene expression was maintained until after 5 days.

TABLE 9

VEGF

| Solutions | Days | Value of intracellular mRNA expression quantification |
|---|---|---|
| — | 0 | 1.0 |
| Hanks-HEPESpH 7.4 | 1 | 3.5 |
| Hanks-HEPESpH 7.4 | 2 | 7.1 |
| Hanks-HEPESpH 7.4 | 3 | 7.5 |
| Hanks-HEPESpH 7.4 | 4 | 7.1 |
| Hanks-HEPESpH 7.4 | 5 | 4.8 |
| Hanks-HEPBSpH 7.4 | 6 | 2.0 |

Example 7

As was in Example 1, after confirming that the adipose tissue-derived mesenchymal stromal cells became confluent, the medium was removed and the cell surface was rinsed with PBS.

After rinsing the cells, the medium was replaced with HBSS-HEPES pH6.5, HBSS-HEPES pH7.0, HBSS-HEPES PH7.4, HBSS-HEPES pH7.8, or HBSS-HEPES pH9.0. The total RNAs were extracted from the cells in each well immediately after replacement (0 hours) and 48 hours thereafter using ISOGEN (manufactured by Nippon Gene Co., Ltd.), and the expression of the VEGF gene was relatively quantified by real-time PCR. The result is shown in Table 10. As shown in Table 10, it was found that the gene expression was maintained in HBSS-HEPES from PH7.0 to pH7.8.

TABLE 10

VEGF

| Solutions | Value of intracellular mRNA expression quantification |
|---|---|
| — | 1.0 |
| Hanks-HEPESpH 6.5 | 3.5 |
| Hanks-HEPESpH 7.0 | 7.1 |
| Hanks-HEPESpH 7.4 | 7.7 |
| Hanks-HEPESpH 7.8 | 7.0 |
| Hanks-HEPESpH 9.0 | 1.8 |

Example 8

As was in Example 1, the adipose tissue-derived mesenchymal stromal cells were cultured in a 12-well plate, and, after confirming that the cells became confluent, the medium was removed and the cell surface was rinsed with PBS.

The rinsed cells were divided into 4 groups each consisting of 3 wells and their culture media were replaced with HBSS-HEPES added with PGE1 (Prostandin manufactured by Maruishi Pharmaceutical. Co., Ltd.) at a concentration of 0 ng/ml, 4 ng/ml, 40 ng/ml, and 400 ng/ml, followed by culturing in an incubator (Example). At 48 hours after the replacement, the culture supernatant was recovered from each well and subjected to protein quantification using QUANTIKINE ELISA Human VEGF (manufactured by R&D Systems, Inc.). Further, the total RNAs were extracted from each well after recovering the culture supernatant using ISOGEN (manufactured by Nippon Gene Co., Ltd.) and then complementary DNA was synthesized using an iScript cDNA synthesis kit (manufactured by Bio-Rad Laboratories). The complementary DNA was used to relatively quantify the VEGF gene expression level by real-time PCR (Rotor-Gene Q manufactured by QIAGEN). The result is shown in Table 11. As shown in Table 11, the relative quantitative value of the mRNA expression level remained substantially constant independently of the addition amount of PGE1. It was found that the protein amount tended to increase in accordance with the addition amount of PGE1. This proved that the culture supernatant having the higher concentration of VEGF could be obtained by replacing the medium with HBSS-HEPES containing PGE1 and performing culturing for 48 hours.

TABLE 11

| PGE1 concentration (ng/mL) | Value of mRNA relative quantification | VEGF concentration (pg/mL) |
|---|---|---|
| 0 | 1.00 | 199.5 |
| 4 | 0.88 | 201.8 |
| 40 | 1.04 | 281.5 |
| 400 | 0.97 | 299.0 |

Example 9

Adipose tissue-derived mesenchymal stromal cells (ASC) extracted by subjecting normal human adipose tissues to an enzyme treatment were cultured using a DME medium (Dulbecco's modified eagle medium manufactured by Gibco, high glucose) including 20% fetal bovine serum (FBS) in a culture flask T75 (manufactured by BD Falcon) as primary culture. The primary culture cells right before confluency were recovered by an enzyme treatment and then appropriately diluted. The diluted cells having an appropriate cell number were seeded on one 6-well culture plate (manufactured by Sumitomo Bakelite Co., Ltd.) using the same medium and cultured until becoming confluent.

The cells having reached confluence in each well were divided into 2 groups each consisting of 3 wells, and each medium was removed and the cell surface in each well was rinsed with PBS (Dulbecco's phosphate buffered saline manufactured by DS Pharma Biomedical Co., Ltd.).

After rising, the first group was added with a DME high glucose medium, the second group was added with HBSS (Hanks' balanced salt solution manufactured by Sigma-Aldrich Co.) adjusted to pH7.4 with HEPES at a final concentration of 10 mM, and the third group was added with HBSS adjusted to pH7.4 with HEPES at a final concentration of 20 mM. After culturing for 48 hours in an incubator (Example), each culture supernatant was recovered in a 5 mL tube (manufactured by BD Falcon) and the VEGF protein was quantified by using QUANTIKINE ELISA Human VEGF (manufactured by R&D Systems, Inc.). Further, the total RNAs were extracted from the cells in each well using ISOGEN (manufactured by Nippon Gene Co., Ltd.) and concentrated. Complementary DNA was obtained using an iScript cDNA synthesis kit (manufactured by Bio-Rad Laboratories). Then, the complementary DNA was used to relatively quantify each expression level of VEGF, FGF2basic, MMP1, EFNA3, BMP1, and WNT5A genes by real-time PCR (Rotor-Gene Q manufactured by QIAGEN). The results are shown in Table 12 to Table 17. The relative quantitative value was calculated by performing normalization among the samples with beta-actin as an internal standard and taking a value in the DME high glucose medium as a reference value. As shown in Table 12 to Table 17, it was found that the expression of each of mRNAs in the cells tended to be higher in the cells cultured in HBSS-10 mM HEPES pH7.4 than the DME medium, and, further, the expression was higher with HEPES at a concentration of 20 mM.

TABLE 12

| VEGF | |
|---|---|
| Media | Value of mRNA (VEGF) relative quantification |
| DME (High glucose) | 1.00 |
| HBSS-10 mM HEPES pH 7.4 | 0.86 |
| HBSS-20 mM HEPES pH 7.4 | 7.41 |

TABLE 13

| FGF2basic | |
|---|---|
| Media | Value of mRNA (VEGF) relative quantification |
| DME (High glucose) | 1.00 |
| HBSS-10 mM HEPES pH 7.4 | 0.95 |
| HBSS-20 mM HEPES pH 7.4 | 1.39 |

TABLE 14

| MMP1 | |
|---|---|
| Media | Value of mRNA (VEGF) relative quantification |
| DME (High glucose) | 1.00 |
| HBSS-10 mM HEPES pH 7.4 | 1.42 |
| HBSS-20 mM HEPES pH 7.4 | 2.39 |

TABLE 15

| EFNA3 | |
|---|---|
| Media | Value of mRNA (VEGF) relative quantification |
| DME (High glucose) | 1.00 |
| HBSS-10 mM HEPES pH 7.4 | 1.04 |
| HBSS-20 mM HEPES pH 7.4 | 1.92 |

TABLE 16

| BMP1 | |
|---|---|
| Media | Value of mRNA (VEGF) relative quantification |
| DME (High glucose) | 1.00 |
| HBSS-10 mM HEPES pH 7.4 | 1.16 |
| HBSS-20 mM HEPES pH 7.4 | 1.46 |

TABLE 17

| Media | Value of mRNA (VEGF) relative quantification |
|---|---|
| DME (High glucose) | 1.00 |
| HBSS-10 mM HEPES pH 7.4 | 1.16 |
| HBSS-20 mM HEPES pH 7.4 | 2.56 |

Example 10

As was in Example 4, the adipose tissue-derived mesenchymal stromal cells (ASC) were seeded on five 6-well culture plates (manufactured by Sumitomo Bakelite Co., Ltd.) and cultured until becoming confluent.

Similarly, stem cells from human exfoliated deciduous teeth (SHED) were seeded on five 6-well plates and cultured until becoming confluent.

The ASC and SHED having reached confluence, the cells in each well were divided into 3 groups each consisting of 2 wells, and each medium was removed and the cell surface in each well was rinsed with PBS (Dulbecco's phosphate buffered saline manufactured by DS Pharma Biomedical Co., Ltd.).

After rising, three groups were each added with 3 mL, 2 mL, or 1 mL of HBSS (Hanks' balanced salt solution manufactured by Sigma-Aldrich Co.)-HEPES pH7.4 and cultured for 48 hours in an incubator (Example). Subsequently, each culture supernatant was recovered in a 5 mL tube (manufactured by BD Falcon) and the VEGF protein was quantified by using QUANTIKINE ELISA Human VEGF (manufactured by R&D Systems, Inc.). Further, the total RNAs were extracted from the cells in each well using ISOGEN (manufactured by Nippon Gene Co., Ltd.) and concentrated. Complementary DNA was obtained using an iScript cDNA synthesis kit (manufactured by Bio-Rad Laboratories). Then, the complementary DNA was used to relatively quantify the VEGF gene expression level by real-time PCR (Rotor-Gene Q manufactured by QIAGEN).

The relative quantitative value was calculated by performing normalization among the samples with beta-actin as an internal standard and taking a value in the 2 mL normal medium as a reference value.

TABLE 18

Result
ASC

| Culture supernatant vol. | Value of mRNA (VEGF) relative quantification | Value of VEGF relative quantification |
|---|---|---|
| 3 mL | 0.96 | 0.85 |
| 2 mL | 1.00 | 1.00 |
| 1 mL | 0.83 | 1.34 |

TABLE 19

SHED

| Culture supernatant vol. | Value of mRNA (VEGF) relative quantification | Value of VEGF relative quantification |
|---|---|---|
| 3 mL | 1.25 | 0.93 |
| 2 mL | 1.00 | 1.00 |
| 1 mL | 0.95 | 1.09 |

The mRNA expression level in the cells did not change by the amount of the culture supernatant. The amount of the VEGF protein included in the culture supernatant was lower with the higher volume of the culture supernatant and higher with the lower volume of the culture supernatant. This proved that the culture supernatant including more growth factors could be obtained by using the medium in a volume smaller than that of the medium of normal use.

Example 11

As was in Example 5, the culture supernatant after 48 hours in the second culturing step was recovered and the culture supernatant obtained by centrifugal separation (740G, 5 minutes) was divided into 2 groups, a no addition group and a group with addition of 250 mM trehalose (manufactured by Hayashibara Co., Ltd.). Subsequently, the culture supernatant was passed through a filtration filter (KURABO INDUSTRIES Ltd.) having a membrane pore diameter of 0.2 micrometers and aliquoted into syringes (Terumo Corp.). The syringes were sealed in sterile bags, frozen in a –80° C. freezer, and then transferred to the inside of the freeze-drying device (Yamato Scientific Co., Ltd.) to perform freeze drying. After the completion of freeze drying, the syringes were sealed with luer caps for syringe (Terumo Corp.). The freeze-dried samples were stored in a sealed state under three temperature conditions of –80° C., 4° C., and 25° for 3 weeks. After 3 weeks, the freeze-dried samples were resuspended in water for injection (manufactured by Otsuka Pharmaceutical Co., Ltd.) and protein quantification was performed using QUANTIKINE ELISA Human VEGF (manufactured by R&D Systems, Inc.). As a quantitative value, a relative quantitative value of the VEGF protein at each storage temperature was calculated by taking a quantitative value of the VEGF protein included in the culture supernatant stored at –80° C. for 3 weeks as a reference. The result is shown in Table 20. As shown in Table 20, it was confirmed that the VEGF protein was significantly reduced in the freeze-dried culture supernatant with no addition after being stored under the environment of 25° C. This suggests protein degradation caused by moisture absorption and photooxidation. On the other hand, it was found that adding trehalose at a final concentration of 250 mM suppressed the reduction of the VEGF protein.

TABLE 20

| | Value of VEGF relative quantification at each storage temperature | | |
|---|---|---|---|
| Additives | –80° C. | 4° C. | 25° C. |
| None | 1.00 | 0.89 | 0.22 |
| 250 mM Trehalose | 1.00 | 0.96 | 0.73 |

Example 12

Adipose tissue-derived mesenchymal stromal cells extracted by subjecting normal human adipose tissues to an enzyme treatment were cultured using a DME medium (Dulbecco's modified eagle medium manufactured by Gibco, high glucose) including 20% fetal bovine serum (FBS) in a culture flask (manufactured by Falcon) as primary culture. The primary culture cells right before confluency were recovered by an enzyme treatment and seeded in five culture flasks T75 (manufactured by BD Falcon) using the same medium and cultured until becoming confluent.

After confirming that the cells became confluent, the medium was removed and the cell surface was rinsed with PBS (Dulbecco's phosphate buffered saline manufactured by DS Pharma Biomedical Co., Ltd.).

After rinsing the cells, the medium was replaced with HBSS (Hanks' balanced salt solution manufactured by Sigma-Aldrich Co.)-HEPES and the cells were cultured for 48 hours in an incubator (Example). Then, the culture supernatants were each recovered in a 20 ml syringe (manufactured by Terumo Corp.) in a volume of 15 mL.

The recovered culture supernatants were freeze dried.

Two culture supernatants freeze dried in the 20 mL syringes were each suspended with 15 mL of water for injection and subjected to a concentration operation to 0.6 mL using VIVASPIN20, VS2041 (manufactured by Sartorius AG) and a centrifugal machine KUBOTA2800 (manufactured by KUBOTA Corp.).

After the concentration operation, one of the culture supernatants was used to isolate and extract exosomes in the culture supernatant in accordance with a conventional method using an Exosome Isolation Kit (manufactured by FUJIFILM Wako Pure Chemical Corp.) (Sample 1). The exosome extract thus extracted had a volume of 0.1 mL. The other culture supernatant was stored as it was in a 1.5 mL tube (manufactured by Eppendorf AG) (Sample 2).

Using the Sample 1 obtained by performing the concentration operation followed by the isolation and extraction of the exosomes and the culture supernatant Sample 2 obtained by performing only the concentration operation, the exosomes included in these samples were relatively quantified in accordance with a conventional method using an Exosome ELISA Kit (manufactured by FUJIFILM Wako Pure Chemical Corp.). The quantitative value was obtained as follows. A difference between an absorbance of 450 nm and an absorbance of 650 nm was determined and normalized using a blank value. On the basis of this absorbance value, the quantitative value was represented as an integrated vale of the absorbance included in the 15 mL culture supernatant. The result is shown in Table 21. As shown in Table 21, by comparing the absorbance values of both samples, it was found that the culture supernatant prepared by the present production method included the exosomes and a considerable amount of the exosomes could be utilized without having the trouble of isolating and extracting the exosomes.

TABLE 21

| Result of exosome relative quantification | |
|---|---|
| | Value of exosome quantification |
| Sample 1 | 116.94 |
| Sample 2 | 150.06 |

Example 13

Adipose tissue-derived mesenchymal stromal cells (ASC) extracted by subjecting normal human adipose tissues to an enzyme treatment were cultured using a DME medium (Dulbecco's modified eagle medium manufactured by Gibco, high glucose) including 20% fetal bovine serum (FBS) in a culture flask T75 (manufactured by BD Falcon) as primary culture. The primary culture cells right before confluency were recovered by an enzyme treatment and then seeded on two 6-well culture plates (manufactured by Sumitomo Bakelite Co., Ltd.) using the same medium and cultured until becoming confluent.

The cells having reached confluence in each well were divided into 2 groups each consisting of 3 wells, and each medium was removed and the cell surface in each well was rinsed with PBS (Dulbecco's phosphate buffered saline manufactured by DS Pharma Biomedical Co., Ltd.).

After rising, two groups were added with 2 mL of HBSS (Hanks' balanced salt solution manufactured by Sigma-Aldrich Co.)-HEPES pH7.4 and cultured for 24 hours or 48 hours in an incubator (Example). After 24 hours or 48 hours, for the first group, the culture supernatant was recovered in a 5 mL tube (manufactured by BD Falcon) as usual. For the second group, the adherent cells were recovered in a 5 mL tube together with the culture supernatant using a cell scraper (manufactured by AGC Inc.) and crushed using Physcotron (manufactured by Nichion Irika Kikai Seisakusho) to prepare measurement samples. In each sample, the VEGF protein was quantified by using QUANTIKINE ELISA Human VEGF (manufactured by R&D Systems, Inc.). A relative quantitative value of the VEGF protein included in the cell-containing culture supernatant was calculated by taking a quantitative value of the VEGF protein obtained from the first group (the culture supernatant) as a reference. The results are shown in Table 22 and Table 23. In Table 23, the relative quantitative value was a value obtained by calculating the relative quantitative value of the VEGF protein included in each sample after 48 hours of culturing by taking the quantitative value of the VEGF protein obtained from the culture supernatant after 24 hours of culturing as a reference. As shown in Table 22 and Table 23, it was found that more growth factors could be utilized by using the cell-containing culture supernatant.

TABLE 22

| Result Culture time: 24 hours | |
|---|---|
| Samples | Value of VEGF relative quantification |
| Culture supernatant | 1.00 |
| Cell-containing culture supernatant | 1.25 |

TABLE 23

| Culture time: 48 hours | | |
|---|---|---|
| Samples | Value of VEGF relative quantification | Value of relative quantification |
| Culture supernatant | 1.00 | 2.90 |
| Cell-containing culture supernatant | 1.26 | 3.65 |

Example 14

From healthy human skin tissue derived epidermal cells, fibroblasts were selectively cultured by a conventional method. The primary culture thus obtained was subjected to maintenance culture and the cells in the fourth passage were seeded on five 6-well plates (manufactured by Sumitomo Bakelite Co., Ltd.) and cultured until becoming confluent. The cells having reached confluence in each well were divided into 2 groups each consisting of 3 wells, and each medium was removed and the cell surface in each well was rinsed with PBS (Dulbecco's phosphate buffered saline manufactured by DS Pharma Biomedical Co., Ltd.). After rising, the media of the first group were each replaced with 2 mL of HBSS (Hanks' balanced salt solution manufactured by Sigma-Aldrich Co.)-HEPES pH7.4, while the media of the second and the third groups were replaced respectively with the same amount of the solutions prepared by adding the culture supernatant derived from the adipose tissue stem cells (ASCsup.) shown in Example 1 to HBSS-HEPES pH7.4 at a final concentration of 10% and 50%. Subsequently, the cells were cultured for 3, 6, 24 or 48 hours in an incubator. The total RNAs were extracted from each well after the lapse of each period of time using ISOGEN (manufactured by Nippon Gene Co., Ltd.). Then, complementary DNA was synthesized using an iScript cDNA synthesis kit (manufactured by Bio-Rad Laboratories) and the complementary DNA was used to relatively quantify the expression levels of the FGFbasic and the VEGF genes by real-time PCR (Rotor-Gene Q manufactured by QIAGEN). A relative quantitative value was calculated by performing normalization among the samples with beta-actin as an internal standard and taking a value of each gene expression level in the cells at the time of confluence as a reference value. The results are shown in Table 24 and Table 25.

TABLE 24

Value of FGF-basic quantification

| Elapsed time | No addition of ASCsup. | Addition of 10% ASCsup. | Addition of 50% ASCsup. |
|---|---|---|---|
| 0 | 1.00 | 1.00 | 1.00 |
| 3 | 0.88 | 0.81 | 1.16 |
| 6 | 0.97 | 1.51 | 1.32 |
| 24 | 2.39 | 1.99 | 2.46 |
| 48 | 2.02 | 2.08 | 2.62 |

TABLE 25

Value of VEGF quantification

| Elapsed time | No addition of ASCsup. | Addition of 10% ASCsup. | Addition of 50% ASCsup. |
|---|---|---|---|
| 0 | 1.00 | 1.00 | 1.00 |
| 3 | 1.14 | 1.31 | 3.94 |
| 6 | 0.93 | 1.39 | 6.57 |
| 24 | 5.78 | 5.17 | 12.47 |
| 48 | 6.92 | 10.27 | 10.78 |

As shown in Table 24 and Table 25, the expression of the FGF-basic gene tended to increase over time until 24 hours after the replacement of the medium but became stationary after 48 hours in the ASC-sup. non-addition group. On the other hand, the expression increased over time until 48 hours after the replacement in the addition group, and the increase rate became higher in a manner dependent on the addition amount.

The expression of the VEGF gene tended to increase over time until 48 hours after the replacement both in the non-addition group and the addition group, and the increase rate became significantly higher in a manner dependent on the addition amount of the ASC-sup.

It was suggested that addition of the culture supernatant of the adipose tissue-derived mesenchymal stromal cells to the fibroblasts promoted the expression of growth factors of their own cells and was effective in tissue regeneration.

Example 15

Healthy human skin tissue derived epidermal cells were extracted by a conventional method and seeded on a 6-well plate. In this operation, the cells were divided into 2 groups: a group in which the EpiLife media was used and a group in which the EpiLife media added with the culture supernatant derived from the adipose tissue stem cells shown in Example 1 was used, and both cells were cultured until becoming confluent. After confirming that the cells became confluent, L-DOPA staining was performed in accordance with a conventional method to quantify color tones of melanocyte stem cells included in the epidermal cells. A quantitative value was obtained based upon the ratio of the area of black portions of the melanocyte stem cells subjected to the L-DOPA staining by using an imaging software ImageJ. The result is shown in Table 26.

TABLE 26

Result

| Media | Average values |
|---|---|
| EpiLife containing original supplements | 1884 |
| EpiLife containing ASC culture supernatant and original supplements | 1174 |

As shown in Table 26, the media added with the culture supernatant derived from the adipose tissue stem cells had the lower quantitative value of the color tones caused by the L-DOPA staining of the melanocyte stem cells present in the epidermal cells, suggesting that the culture supernatant derived from the adipose tissue stem cells had a function of suppressing proliferation and differentiation into the melanocytes of the melanocyte stem cells. This proved that the culture supernatant was effective as a skin-lightening component.

Example 16

A freeze-dried product of the culture supernatant was produced with Example 5. The freeze-dried culture supernatant produced using 1 ml of the culture supernatant was dissolved in 1 ml of two hyaluronic acid preparations, namely, Restylane Lido (manufactured by Galderma) and Belotero (manufactured by Merz Pharma). It was found that the freeze-dried culture supernatant could be dissolved in hyaluronic acid. Thus, when hyaluronic acid was used for subcutaneous administration, intraarticular administration, or the like, the freeze-dried culture supernatant could be administered with hyaluronic acid, allowing the freeze-dried culture supernatant to be used as a raw material of medicines.

Example 17

A freeze-dried product of the culture supernatant was produced with Example 5. The freeze-dried culture supernatant produced using 1 ml of the culture supernatant was dissolved in 1 ml of distilled water and used as cosmetics, foods, and drinks. Further, it was dissolved in 1 g of Hirudoid Soft Ointment (manufactured by Maruho Co., Ltd.), which was a hydrophilic ointment, and then used as an ointment. This showed that the culture supernatant could be used as a raw material of cosmetics, medicines, foods, and drinks.

INDUSTRIAL APPLICABILITY

The present invention can be used in pharmaceutical industries.

The invention claimed is:

1. A method for producing a culture supernatant preparation, said method comprising:
   a first culturing step of culturing a cell to a confluent state using a first medium;
   a second culturing step of culturing the cell using a second medium that is different from the first medium after the first culturing step; and
   a culture supernatant preparation obtaining step of obtaining the culture supernatant preparation including the second medium after the second culturing step,
   wherein the second medium is an infusion liquid for injection or an infusion liquid for intravenous drip infusion.

2. The method for producing the culture supernatant preparation according to claim 1, wherein the second medium further includes prostaglandin.

3. The method for producing the culture supernatant preparation according to claim 1, wherein the culture supernatant preparation obtaining step includes a step of adding trehalose.

4. The method for producing the culture supernatant preparation according to claim 1, wherein the culture supernatant preparation obtaining step further comprises adjusting the contents of the culture supernatant preparation such that the culture supernatant preparation includes the second medium in an amount of from 50 wt. % to 100 wt. %, both inclusive.

5. The method for producing the culture supernatant preparation according to claim 1, wherein the cell is an adipose tissue-derived mesenchymal stromal cell, an epidermis-derived epithelial cell, or a dental pulp-derived mesenchymal stem cell.

6. The method for producing the culture supernatant preparation according to claim 1, wherein, the second culturing step includes culturing the cell for 5 hours or more and 5 days or less.

7. The method for producing the culture supernatant preparation according to claim 1, further comprising:
   a freezing step of freezing the culture supernatant preparation.

8. The method for producing the culture supernatant preparation according to claim 1, wherein the second medium includes a calcium ion and a buffering agent.

9. The method for producing the culture supernatant preparation according to claim 1, wherein the second medium is HBSS (Hanks' balanced salt solution)-HEPES (hydroxyethylpiperazine ethane sulfonic acid) medium.

10. The method for producing the culture supernatant preparation according to claim 9, wherein the HBSS (Hanks' balanced salt solution)-HEPES (hydroxyethylpiperazine ethane sulfonic acid) medium comprises a sodium hydrogen carbonate solution, NaCl, KCl, $MgSO_4 \cdot 7H_2O$, $Na_2HPO_4$, glucose, $KH_2PO_4$, a $CaCl_2$) solution and a hydroxyethylpiperazine ethane sulfonic acid.

11. The method for producing the culture supernatant preparation according to claim 9, wherein the pH of the HBSS (Hanks' balanced salt solution)-HEPES (hydroxyethylpiperazine ethane sulfonic acid) medium is 7.4.

* * * * *